(12) United States Patent
Korlach et al.

(10) Patent No.: US 8,846,881 B2
(45) Date of Patent: *Sep. 30, 2014

(54) MODULAR NUCLEOTIDE COMPOSITIONS AND USES THEREFOR

(75) Inventors: Jonas Korlach, Newark, CA (US); Jeffrey Wegener, Cupertino, CA (US)

(73) Assignee: Pacific Biosciences of California, Inc., Menlo Park, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/552,952

(22) Filed: Jul. 19, 2012

(65) Prior Publication Data

US 2013/0022968 A1   Jan. 24, 2013

Related U.S. Application Data

(63) Continuation of application No. 12/621,352, filed on Nov. 18, 2009, now Pat. No. 8,252,910.

(60) Provisional application No. 61/116,202, filed on Nov. 19, 2008.

(51) Int. Cl.
*C07H 15/00* (2006.01)
*C07H 19/04* (2006.01)
*C12Q 1/68* (2006.01)
*C12P 19/34* (2006.01)

(52) U.S. Cl.
USPC .............. 536/4.1; 536/26.6; 435/5; 435/6.1; 435/7.1; 435/7.2; 435/91.1

(58) Field of Classification Search
USPC ......... 536/4.1, 26.6; 435/5, 6.1, 7.1, 7.2, 91.1
See application file for complete search history.

(56) References Cited

U.S. PATENT DOCUMENTS

| | | |
|---|---|---|
| 4,711,955 A | 12/1987 | Ward et al. |
| 5,328,824 A | 7/1994 | Ward et al. |
| 5,476,928 A | 12/1995 | Ward et al. |
| 5,547,839 A | 8/1996 | Dower et al. |
| 5,688,648 A | 11/1997 | Mathies et al. |
| 5,733,743 A | 3/1998 | Johnson et al. |
| 6,210,896 B1 | 4/2001 | Chan |
| 6,255,083 B1 | 7/2001 | Williams |
| 6,399,335 B1 | 6/2002 | Kao et al. |
| 6,787,308 B2 | 9/2004 | Balasubramanian et al. |

(Continued)

FOREIGN PATENT DOCUMENTS

| | | |
|---|---|---|
| WO | 9106678 A1 | 5/1991 |
| WO | 9627025 A1 | 9/1996 |
| WO | 9905315 A2 | 2/1999 |
| WO | 2007076057 A2 | 7/2007 |

OTHER PUBLICATIONS

Eid, et al., "Real-time DNA sequencing from single polymerase molecules" Science (2009) 323(5910):133-138.

(Continued)

*Primary Examiner* — Jezia Riley
(74) *Attorney, Agent, or Firm* — Deana A. Arnold

(57) ABSTRACT

Nucleic acid compositions, methods of making and using such compositions that comprise modular functional groups that can be configured to provide desired functionality to different nucleotide types, through a swappable and preferably non-covalent linkage component. Such compositions are useful in a variety of applications including nucleic acid analyses.

14 Claims, 8 Drawing Sheets

(56) References Cited

U.S. PATENT DOCUMENTS

| | | | |
|---|---|---|---|
| 7,033,764 | B2 | 4/2006 | Korlach et al. |
| 7,041,812 | B2 | 5/2006 | Kumar et al. |
| 7,052,847 | B2 | 5/2006 | Korlach et al. |
| 7,056,661 | B2 | 6/2006 | Korlach et al. |
| 7,056,676 | B2 | 6/2006 | Korlach et al. |
| 7,361,466 | B2 | 4/2008 | Korlach et al. |
| 7,405,281 | B2 | 7/2008 | Xu et al. |
| 7,416,844 | B2 | 8/2008 | Korlach et al. |
| 7,427,673 | B2 | 9/2008 | Balasubramanian et al. |
| 2003/0044781 | A1 | 3/2003 | Korlach |
| 2003/0077610 | A1 | 4/2003 | Nelson et al. |
| 2003/0096253 | A1 | 5/2003 | Nelson et al. |
| 2003/0124576 | A1 | 7/2003 | Kumar et al. |
| 2003/0162213 | A1 | 8/2003 | Fuller et al. |
| 2003/0190647 | A1 | 10/2003 | Odera |
| 2003/0215862 | A1 | 11/2003 | Parce et al. |
| 2004/0048300 | A1 | 3/2004 | Sood et al. |
| 2004/0152119 | A1 | 8/2004 | Sood et al. |
| 2004/0224319 | A1 | 11/2004 | Sood et al. |
| 2004/0241716 | A1 | 12/2004 | Kumar et al. |
| 2005/0095627 | A1* | 5/2005 | Kolman et al. ............ 435/6 |
| 2005/0208557 | A1 | 9/2005 | Korlach et al. |
| 2007/0048773 | A1 | 3/2007 | Lee et al. |
| 2009/0162845 | A1 | 6/2009 | Rabbani et al. |
| 2009/0186343 | A1 | 7/2009 | Wang et al. |
| 2011/0165652 | A1 | 7/2011 | Hardin et al. |

OTHER PUBLICATIONS

Guranowski, A. "Metabolism of Diadenosine Tetraphosphate (Ap4A) and Related Nucleotides in Plants: Review with Historical and General Perspective" Frontiers in Bioscience (2004) 9:1398-1411.

Levene et al., "Zero-mode waveguides for single-molecule analysis at high concentrations" Science (2003) 299 (5607):682-686.

Lundquist et al. "Parallel Confocal Detection of Single Molecules in Real Time" Opt Lett (2008) 33(9):1026-1028.

International Search Report issued Jun. 21, 2010 for corresponding PCT application PCT/US2009/006177 filed Nov. 18, 2009.

International Preliminary Report on Patentability issued Jun. 3, 2011 for corresponding PCT application PCT/US2009/006177 filed Nov. 18, 2009.

* cited by examiner

MODULAR NUCLEOTIDE COMPOSITIONS AND USES THEREFOR

CROSS-REFERENCE TO RELATED APPLICATIONS

This application is a continuation application of U.S. Nonprovisional application Ser. No. 12/621,352, filed Nov. 18, 2009, which claims the benefit of U.S. Provisional Application No. 61/116,202, filed Nov. 19, 2008, the disclosure of which is incorporated herein by reference in its entirety for all purposes.

STATEMENT REGARDING FEDERALLY SPONSORED RESEARCH

Not Applicable.

INCORPORATION-BY-REFERENCE OF MATERIAL SUBMITTED BY U.S.P.T.O. eFS-WEB

The instant application contains a Sequence Listing which is being submitted in computer readable form via the United States Patent and Trademark Office eFS-WEB system, and is hereby incorporated by reference in its entirety for all purposes. The txt file submitted herewith contains only one 2 KB file (01007602_2012-10-02_SequenceListing.txt).

BACKGROUND OF THE INVENTION

A wide variety of nucleotide compositions and nucleotide analog compositions have been provided for use in a variety of different applications. In some cases, these compositions function as analytical reagents for the analysis of biological processes, e.g., in nucleic acid sequencing reactions. In other cases, these compositions function as pharmaceutically active substances for the treatment of disease. In still other aspects, these compositions form building blocks for other commercial applications. In a number of situations, a basic nucleotide, e.g., a nucleoside triphosphate, is coupled to an additional functional group in order to provide an additional or a different function to that compound. For example, in one of the more ubiquitous embodiments, detectable label groups, such as fluorescent dyes, radiolabels, semiconductor nanocrystals, or the like, are coupled to the nucleotide to render the nucleotide more easily detectable, e.g., through a fluorescent microscope. These labels may be coupled to persistent components of the nucleotide, i.e., the nucleobase, that remains even following polymerization with other nucleotides, or they may be coupled through the transient portions, e.g., a gamma phosphate group that may be removed upon polymerization. In other cases, functional groups may be coupled to nucleotides or nucleotide analogs in order to provide therapeutic activity, e.g., in interrupting viral replication, or the like.

Despite the widespread use of functionally tagged nucleotides, it would be desirable to provide for a modular nucleotide composition that allows simple and flexible functionalization of nucleotides for use in a variety of different applications. The present invention meets these and other needs.

BRIEF SUMMARY OF THE INVENTION

The invention generally provides modular nucleotide compositions and methods of making and using such compositions that employ a cassette approach to addition of functional groups to nucleotide analogs.

In certain aspects, the present invention provides a composition having a nucleoside polyphosphate coupled to a functional group through a phosphate group by a non-covalent linkage. In certain embodiments, the functional group is coupled to the nucleoside polyphosphate through a phosphate group other than the alpha phosphate group, e.g., the beta, gamma, or other terminal phosphate group. In preferred embodiments, the functional group comprises a detectable label, such as a fluorescent label. In certain embodiments, the functional group is a "payload" delivered by the composition, e.g., a pharmaceutical compound or diagnostic agent. In certain embodiments, the functional group comprises a particle, e.g., a magnetic particle, a fluorescent semiconductor particle, a metal particle, and/or a polymeric particle.

The non-covalent linkage preferably comprises one or more of an affinity linkage, biotin, avidin (or biotin-binding subunit thereof), streptavidin (or biotin-binding subunit thereof), neutravidin (or biotin-binding subunit thereof), an antibody or fraction thereof, a polynucleotide, a nucleic acid binding protein, or a combination thereof. In certain embodiments, the non-covalent linkage is a polyvalent non-covalent linkage. For example, a polyvalent non-covalent linkage may couple multiple functional groups to a single nucleoside polyphosphate, or may couple multiple nucleoside polyphosphates to a single functional group, of may couple multiple nucleoside polyphosphates to multiple functional groups. The multiple nucleotide polyphosphates and/or multiple functional groups can be the same or different from one another. For example, multiple functional groups can comprise spectrally distinguishable fluorescent labels or moieties with different charges.

In certain embodiments, the invention provides compositions having multiple non-covalent linkages. For example, in some compositions of the invention multiple non-covalent linkages couple a single nucleoside polyphosphate to multiple functional groups, and in other compositions of the invention multiple non-covalent linkages couple multiple single nucleoside polyphosphates to a single functional group.

In other aspects, the invention provides compositions having the structure BSPLF, where B comprises a nucleobases moiety, S comprises a sugar, acyclic, or carbocyclic moiety, P comprises a polyphosphate group, L comprises a non-covalent linkage component, and F comprises a desired functional group. In certain preferred embodiments, L comprises an affinity binding pair.

In further aspects, the invention provides methods for preparing nucleotide compositions that include providing a nucleoside polyphosphate having a first non-covalent linking group coupled to a phosphate group; providing a functional group having a second non-covalent linking group coupled thereto, the second non-covalent linking group being capable of non-covalently binding to the first non-covalent linking group; and linking the nucleoside polyphosphate to the functional moiety through the first and second non-covalent linking groups. Preferably, the phosphate group through which the non-covalent linking group is coupled to the nucleoside polyphosphate is hot the alpha phosphate group of the nucleoside polyphosphate. In preferred embodiments, the first and second non-covalent linking groups form an affinity binding pair, e.g., an epitope pair, GST/glutathione pair, RNA/aptamer pair, or an associative protein or polypeptide pair. For example, in some embodiments the first non-covalent linking group is complementary to the second non-covalent linking group. In other embodiments, one of the non-covalent linking groups is an antibody and the other is an antigen. In yet further embodiments, one of the non-covalent linking groups is a nucleic acid and the other is a nucleic acid binding protein.

In yet further aspects; the invention provides systems for providing functionalized nucleotide compositions comprising: a first source of nucleoside polyphosphates having at least a first linkage component attached to a phosphate group thereon; a second source of functional groups having a second linkage component coupled thereto, wherein the first and second linkage components comprise an affinity binding pair. The system can further include a reagent mixing system for transferring nucleoside polyphosphate from the first source and functional; groups from the second source to a mixing chamber to combine the nucleoside polyphosphate and the functional groups under conditions whereby the first and second linkage components form a non-covalent linkage, thereby providing functionalized nucleotide compositions. The system can further include a dispensing the functionalized nucleotide compositions into a reaction mixture. In preferred embodiments, the first source comprises at least two different nucleoside polyphosphates having the first linkage component attached to a phosphate group thereon; and/or the second source comprises at least two different functional groups having the second linkage component coupled thereto. The system is capable of providing multiple different functionalized nucleotide compositions, each of which comprises the first and second linkage component and a different combination of nucleoside polyphosphate and functional group. For example, each may comprise the same avidin/biotin pair, but a different combination of nucleoside polyphosphate and detectable label.

DETAILED DESCRIPTION OF THE INVENTION

Figure 1:
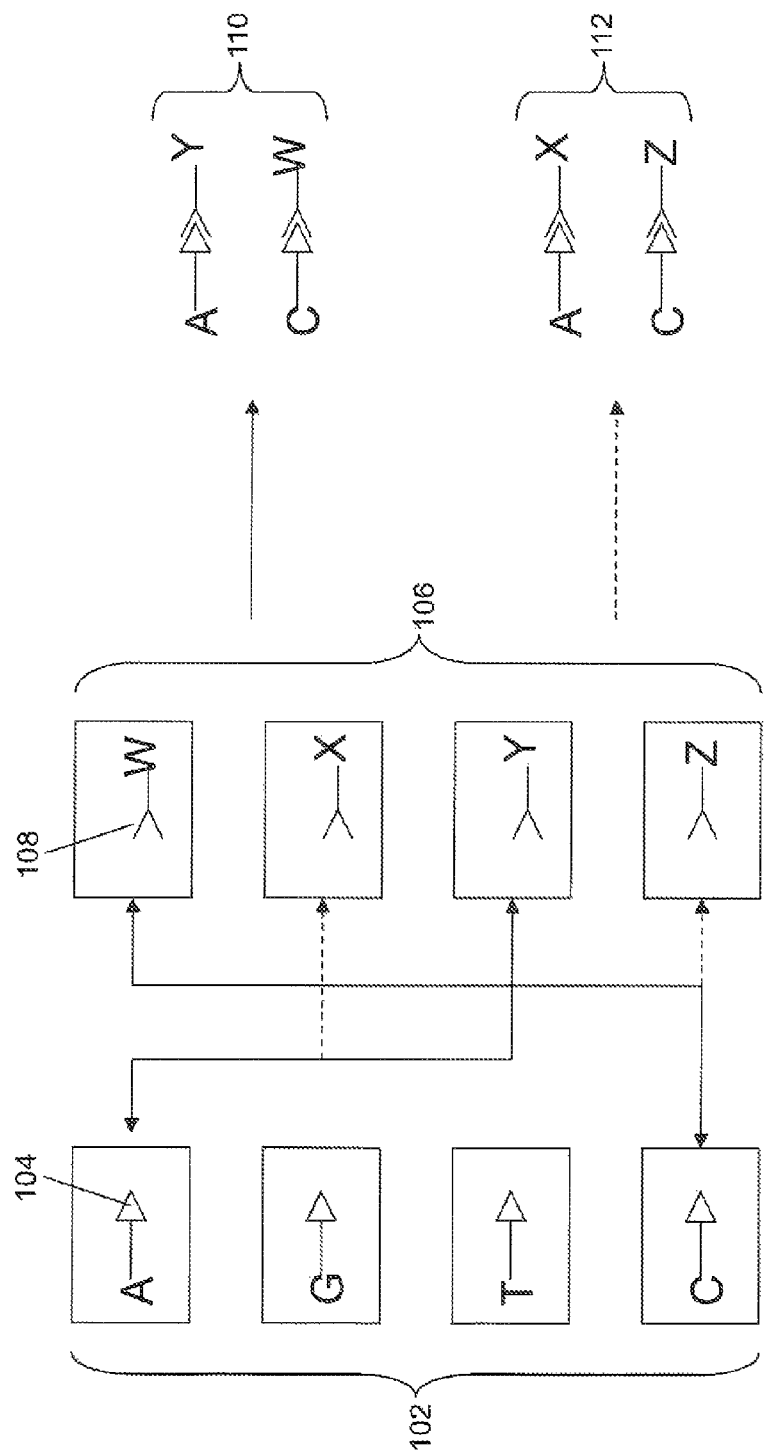
FIG. 1 schematically illustrates modular nucleotide compositions of the invention.

The present invention provides novel nucleotide compositions and methods for their use in a variety of different applications, such as genetic analysis, pharmaceutical research, medical diagnostics, and even in the treatment of different disorders. The present invention is characterized by nucleotide compositions that include functional groups coupled to such nucleotides through novel linkages that permit flexible development and use of a wide range of alternative compositions, all of which fall within the scope of the invention.

The compositions of the present invention are generally characterized in that they comprise a nucleoside polyphosphate or analogous structure, and carry a functional group coupled to one or more of the phosphate groups in the phosphate chain using a configurable linkage.

While other compositions have proposed coupling certain types of functional groups to the gamma or other phosphate groups in the polyphosphate chain (See, e.g., U.S. Pat. Nos. 6,399,335, 6,056,661, 7,052,847, 7,033,764, 7,056,676, 7,361,466, 7,416,844, the full disclosures of which are incorporated herein by reference in their entirety for all purposes), the compositions of the present invention may be characterized by either or both of coupling novel functional groups to the basic nucleotide structure and/or by coupling such functional groups through a linkage that permits ready interchangeability of the functional groups based upon a desired use or application. The resulting nucleotide compositions are thus modular, in that they can easily swap out nucleotide component and functional component, without the need for complex synthesis processes.

In accordance with the present invention, the nucleotide compositions described herein comprise the basic structure:

B-S-P-L-F where B refers to a nucleobase moiety;

S comprises a sugar moiety, an acyclic moiety of a carbocyclic moiety;

P comprises a polyphosphate group;

L comprises a configurable linker component; and

F comprises a desired functional group.

As alluded to above, the combination of the B and S groups typically comprises any of a variety of nucleoside compositions, including for example, ribonucleosides, deoxyribonucleosides, dideoxyribonucleosides, and the like. Also included are alternative nucleoside structures, such as locked nucleosides, and the like. Notwithstanding the foregoing, with respect to; the specific components, it will be appreciated that in the compounds of the invention, the S group is preferably a sugar moiety that provides a suitable backbone for a synthesizing nucleic acid strand. In it most preferred aspect, the sugar moiety is selected from a D-ribosyl, 2' or 3' D-deoxyribosyl, 2',3'-D-dideoxyribosyl, 2',3'-D-didehydrodideoxyribosyl, 2' or 3' alkoxyribosyl, 2' or 3' aminoribosyl, 2' or 3' mercaptoribosyl; 2' or 3' alkothioribosyl, acyclic, carbocyclic or other modified sugar moieties. A variety of carbocyclic or acyclic moieties may be incorporated as the "S" group in place of a sugar moiety, including, e.g., those described in published U.S. Patent Application No. 2003/0124576, previously incorporated herein by reference in its entirety for all purposes.

As noted previously, the base moiety (B) incorporated into the compounds of the invention is generally selected from any of the natural or non-natural nucleobases or nucleobase analogs, including, e.g., purine or pyrimidine bases that are routinely found in nucleic acids and nucleic acid analogs that are well known in the art, including, for example, adenine, thymine, guanine, cytidine, uracil, and in some cases, inosine. For purposes of the present description, nucleotides and nucleotide analogs are generally referred to based upon their relative analogy to naturally occurring nucleotides. As such, an analog that operates, functionally, like adenosine triphosphate, may be generally referred to herein by the shorthand letter A. Likewise, the standard abbreviations of T, G, G, U and I, may be used in referring to analogs of naturally occurring nucleosides and nucleotides typically abbreviated in the same fashion. In some cases, a base may function in a more universal fashion, e.g., functioning like any of the purine bases in being able to hybridize with any pyrimidine base, or vice versa. The base moieties used in the present invention may include the conventional bases described herein or they may include such bases substituted at one or more side groups, of other fluorescent bases or base analogs, such as 1,N6 ethenoadenosine of pyrrolo C, in which an additional ring structure renders the B group neither a purine nor a pyrimidine. For example, in certain cases, it may be desirable to substitute one or more side groups of the base moiety with a labeling group or a component of a labeling group, such as one of a donor or acceptor fluorophore, or other labeling group. Examples of labeled nucleobases and processes for labeling such groups are described in, e.g., U.S. Pat. Nos. 5,328,824 and 5,476,928, each of which is incorporated herein by reference in its entirety for all purposes.

The polyphosphate component (P) of the compositions of the present invention typically refers to a chain of phosphate groups coupled by phosphodiester linkages. While in nucleoside triphosphates, these phosphate chains will comprise three phosphate groups, it will be appreciated that in the context of the present invention, the phosphate chains will comprise anywhere from two to seven phosphate groups, e.g., a diphosphate, triphosphate, tetraphosphate, pentaphosphate, hexaphosphate, or heptaphosphate.

Further, although described in terms of phosphate groups, it will be appreciated that the polyphosphate component may include a variety of variations from naturally occurring polyphosphate portions of nucleotides, including, e.g., phosphonate or other linkages between phosphates (See, e.g., U.S. Pat. No. 7,405,281, incorporated herein by reference in its entirety for all purposes), as well as substitution at various side chains to such phosphate groups. For the most part, such variations will be selected such that the compositions still retain the desired biological activity, e.g., as substrates for polymerases, kinases, or other enzymes, or otherwise as the particular application requires.

The functional group (F) is coupled to the nucleotide composition through the polyphosphate chain (P). In preferred aspects, the functional group is coupled to one of the phosphate groups beyond the alpha phosphate, i.e., the phosphate group immediately coupled to the nucleoside. For example, the functional group can be coupled to the beta, gamma or more distal phosphate group. By providing the functional group at other than the alpha phosphate group, these compositions provide for convenient removal of the functional group during normal biological processes, e.g., nucleic acid polymerization, or other catalytic operations. In certain preferred aspects, the functional group is coupled to the terminal phosphate in the polyphosphate chain, i.e., the phosphate group furthest from the nucleoside portion.

Coupling of the linkage group to the phosphate group in the polyphosphate chain may be accomplished by a variety of methods known in the art. For example, such coupling may comprise O, S, N, in ether, ester, amine, amide, thio or other linkages. In addition to the initial linkage, it will be appreciated that additional components may also be included in coupling the linkage component to the polyphosphate chain, such as polymeric or other conventionally employed linker groups, such as alkyl groups, polyalcohols, polyethylene glycols, polyamino acids, etc. (See Provisional Patent Application Nos. 61/069,247, filed Mar. 13, 2008, and No. 61/026,992, filed Mar. 7, 2008, the full disclosures of each of which are hereby incorporated hereby reference in their entirety for all purposes) to provide additional benefits to the composition.

In the present invention, me functional group is coupled to the polyphosphate groups through a configurable linkage that allows in situ attachment of the functional group to the polyphosphate chain. In particular the linkage included within the compositions of the invention allows for a cassette approach to the selection and configuration of nucleotides in order to tailor such compositions for a desired application. This cassette approach takes advantage of a facile linkage process which does not require the use of complex synthetic schemes to covalently couple functional groups to nucleotide compositions. Use of such facile linkage processes permits one to rapidly choose and link a desired functional group to a nucleotide for use in a desired application. Further, one can configure sets of nucleotides according to a wide variety of application specific criteria. A schematic illustration of the cassette-based linkage process is illustrated in FIG. 1.

In a first preferred aspect, this linkage constitutes a non-covalent linkage between the polyphosphate chain and the functional group. While described as a non-covalent linkage, it will be appreciated that such description does not necessarily preclude the option that such linkage could be rendered covalent at a subsequent time, through additional treatments.

In particularly preferred aspects, the linkage component (L) comprises two members of a specific associating pair of moieties that couple the functional group to the nucleotide through a non-covalent linkage. Use of a swappable linkage permits a nucleotide composition to be readily configured with different types of functional groups through the use of the same type of linkage component. This modular approach to configuring nucleotide compositions is schematically illustrated in FIG. 1. In particular, shown are four nucleotides or nucleotide analogs 102 (including A, G, T and C), each configured with one half of a linkage component 104, e.g., one member of an affinity binding pair. A set of functional groups 106 (denoted as W, X, Y and Z) are then provided with the complementary linkage component 108. Combination of nucleotides, with a first set of functional groups yields a first set of functionalized nucleotides 110, as indicated by the solid arrows. Alternatively, combination of the same nucleotides with a different set of functional groups yields a different set of functionalized nucleotides 112 (as indicated by the dashed arrows).

A wide variety of different types of functional groups maybe coupled to nucleotide components in accordance with the compositions of the invention. For example, the functional groups may include labeling groups. Such labeling groups may be optically detectable, electrically detectable, enzymatically detectable, electrochemically detectable or detectable based upon their mass. Examples of preferred optically detectable labels include, e.g., organic fluorescent labels such as cyanine-, fluorescein-, and/or rhodamine-based dyes, inorganic labels such as semiconductor nanocrystals, or quantum dots. A wide variety of such detectable labels are generally commercially available (See, e.g., the Molecular Probes Handbook, available at online at probes.invitrogen.com/handbook/). Such labels may be incorporated onto a given molecule alone or in an, interactive combination, e.g., as an energy transfer pair such as a donor/quencher pair or a FRET pair. For example, in certain embodiments, the functional groups comprise FRET pairs as described in U.S. Patent Application No. 61/164,567, filed Mar. 30,2009, the disclosure of which is incorporated herein by reference in its entirety for all purposes. Additionally, such labels may comprise organic label materials, e.g., organic fluorophores or inorganic-fluorescent or luminescent compounds, such as semiconductor nanocrystals, i.e., fluorescent quantum dots, or the like.

Alternative labeling groups may also be employed as the functional groups, such as mass labels, e.g., particle or other large moieties that provide detectable variations in mass of the molecule to which they are attached or vary the molecule's rotational diffusion, electrochemical labels, e.g., that detectably alter the charge of the molecule, magnetic labels, such as magnetic, particles, or the like. Other examples of functional groups include conductance affecting groups, i.e., groups that enhance impedance or conductance of the composition, and would be useful in applications where incorporation is detected by changes in impedance at or near the synthesis complex, e.g., in nanopore-based sequencing applications. Examples of conductance impacting functional groups include, e.g.: long alkane chains which optionally include solubility enhancing groups, such as amido substitutions; long polyethylene glycol chains; polysaccharides; particles, such as latex, silica, polystyrene, metal, semiconductor, of dendrimeric particles; branched polymers, such as branched alkanes, branched polysaccharides, branched aryl chains. Other examples of functional groups include particles that are optically detectable through their ability to scatter light. Such particles include any of the particle types described elsewhere, herein, and particularly, metal nanoparticles, e.g., gold, silver, platinum, cobalt, of the like, which may be detected based upon a variety of different light scatter detection schemes, e.g., Rayleigh/Mie light scattering, surface enhanced Raman scattering, or the like. Other particle types may include, e.g., magnetic particles, that may be sensed through appropriate means, e.g., magneto-tunnel junction sensors, etc.

Functional groups may additionally of alternatively include electrochemical groups that may be detected or otherwise exploited for their electrochemical properties, such as their overall electric charge. For example, one may include highly charged groups as the functional group, like additional phosphate groups, sulfate group(s), amino acid groups or chains, e.g., polylysine, polyarginine, etc. Likewise, one may include redox active groups, such as redox active compounds, e.g., heme, of redox active enzymes.

Other functional groups may be selected for their influence on the overall system, rather than their detectability. For example, in the case of nucleic acid polymerase interactions, one may include effectors of that interaction as the functional group, or at least a portion of the functional group. By way of example, one may include as at least a portion of the functional group, metal ion chelators that may directly modulate the presence of divalent metal ions around the polymerase enzyme, and thereby modulate the activity of the enzyme. Examples of such chelators include, e.g., ethylene diamine, ethylene diamine tetraacetic acid (EDTA), poly-EDTA, dimercaprol, or the like. Alternatively, other effectors, such as triplet state quenchers, antioxidants, or other protective agents may be included, as described elsewhere herein.

In still other cases, functional groups may be selected as simply a "payload" for delivery by the nucleotide compositions of the invention. In particular, pharmaceutical compounds may be attached to the nucleotide compositions as a pro-drug that is then released upon metabolization, e.g., DNA replication. Additionally, compounds that are targeted for high replication rate cells or organisms, e.g., tumor cells of viruses, may be attached as the functional group to more specifically target such cells. Examples of such compounds include, e.g., thalidomide, taxol, and the like. Likewise, diagnostic agents, such as contrast dyes or radiolabels, may be specifically delivered to desired regions using the compositions of the invention by attaching such agents to as the functional groups.

Other functional groups include energetic compounds, such as ATP, ADP or AMP, which maybe used to drive other functions, such as enzymatic activity, either at the desired location, or as a detection mechanism, e.g., using released ATP as a driver for a luminescent reaction, e.g., luciferase.

In still other cases, the functional groups may be used to control the reactivity of the composition, e.g., as a caging group that prevents the incorporation of the nucleotide until acted upon by an external trigger, e.g., elevated temperature, optical deprotection, or the like. Such compounds may be used to control the initiation and/or continuation of nucleic acid synthesis.

Other functional groups may also be employed, such as biologically active functional groups, e.g., enzymes, receptors, ligands, cofactors, antibodies or their components, luminescent compounds, chromogenic compounds, structural components, e.g., microscale particles or beads, or the like. The functional groups may additionally or alternatively comprise derivatizable groups, e.g., for coupling further groups to the nucleotide, additional configurable linking groups, e.g., affinity binding groups like those described above as the linking groups (L), etc.

In certain particularly preferred aspects, the compositions of the invention may be exploited to configure different nucleotides with different detectable labels or groups of labels to optimize detection for a given application by providing one member of an affinity binding pair coupled to the nucleotides used in the application, while the various different labeling groups are each coupled to the other member of the affinity binding pair. One can then employ a menu approach in selecting a particular nucleotide to be coupled to a selected label group, and join the two through the linkage component.

As an alternative and/or in addition to variations in labeling configurations, it will be appreciated that a wide variety of other variations may be practicable using the configurable linkage components described herein to serve the needs of the application to which the compositions are to be put.

As still another example, linkage components employing the same affinity binding pairs may be used to configure the overall linkage or connection between the nucleotide and the functional group. In particular, linkages having varying linker lengths, varying linker chemical compositions, e.g., hydrophilic, hydrophobic, polar, charged, neutral, etc., linkers having varying structural characteristics, e.g., rigidity, may be provided by employing a menu of functional groups having such varied linkers coupled there to and bearing a complementary affinity binding pair member to couple to the nucleotide portion.

A wide variety of readily configurable non-covalent linkages may be employed in the compositions of the invention. In particular, a wide-variety of associative coupling pairs may be employed on either end of the linkage to provide for the desired association between the nucleotide portion of the composition and the functional group portion.

In particularly preferred aspects, the linkage constitutes two members of an affinity binding pair. For purposes of the present invention, an affinity binding pair will typically possess a dissociation constant of less than $1 \times 10^{-3}$ M, preferably less than $1 \times 10^{-4}$ M, less than $1 \times 10^{-5}$ M, less than $1 \times 10^{-6}$ M, less than $1 \times 10^{-7}$ M, less than $1 \times 10^{-8}$ M, less than $1 \times 10^{-9}$ M, less than $1 \times 10^{-10}$ M, and in some particularly preferred cases, less than $1 \times 10^{-15}$ M. In most preferred aspects, the dissociation constant of the affinity coupling will be between $1 \times 10^{-5}$ M and $1 \times 10^{-16}$ M, depending upon the application for which the compositions are desired.

A variety of affinity binding pairs are readily applied to the compositions of the invention and include, for example, avidin/biotin pairs (including, e.g., avidin, neutravidin and streptavidin, or associative fragments or subunits thereof), antibody/antigen or epitope pairs, complementary nucleic acid pairs, nucleic acid and nucleic acid binding protein pairs, associative protein or polypeptide pairs, carbohydrate/lectin pairs, GST/glutathione pairs, RNA/aptamer pairs, and the like. By way of example, the dissociation constant of avidin/biotin has been reported at approximately $1 \times 10^{-15}$ (Livnah O, Bayer E A. et al (1993), Proc Natl Acad Sci USA. 90(11):

5076-5080). Certain streptavidin mutants (N23A, S27D) have shown lower affinity but still are capable of readily binding (e.g., $K_d=7\times10^{-5}$ M) (See, Howarth et al., Nat Methods. 2006 April; 3(4): 267-273. By comparison, other affinity binding pairs that may be exploited as linkage components include RNA-aptamers with Kd reported to $330\times10^{-9}$ M (See, Nucleic Acids Res. 1996 Mar. 15; 24(6): 1029-36); and RNA Inhibitor protein:angiogenin pairs that have affinities on the order of, if not greater than biotin:avidin (a reported Kd of less than $10^{-15}$ M). Other types of affinity binding pairs are known in the art. Further, methods for the production of members of specific binding pairs are provided in the art, e.g., in U.S. Pat. No. 5,733,743, incorporated herein by reference in its entirety for all purposes.

The linkage may comprise a simple monovalent linkage, e.g., one nucleotide to one functional group, e.g., as shown in FIG. 1, or it may provide a polyvalent or multivalent linkage where one could couple a single nucleotide to multiple functional groups or multiple nucleotides to a single functional group.

In an example of a monovalent linkage, a nucleic acid linkage may be employed, e.g., as described in Provisional U.S. Patent Application No. 61/069,247, filed Mar. 13, 2008, and previously incorporated herein by reference in its entirety for all purposes. By way of example, a nucleotide may be coupled, through its polyphosphate chain, to a single stranded polynucleotide. A complementary polynucleotide segment is provided coupled to the desired functional group. Mixture of the two components under annealing conditions, then results in the annealing of the two polynucleotide segments and the joining of the functional group to the nucleotide portion.

As noted previously, polyvalent or multivalent, linking groups are also envisioned for use in conjunction with the modular structures of the invention. Use of multivalent linking groups provides numerous additional advantages for a variety of applications. For example, one can tether multiple nucleotides to a single functional group, e.g., a detectable label. As a result, one effectively increases the concentration of the nucleotide without increasing the concentration of the functional group, e.g., the label. In such cases, the concentration increase for nucleotides is not accompanied by an increase in the level of background label that might interfere with the reaction. By contrast, one may also increase the number of functional groups coupled to a single nucleotide, e.g., providing multiple labeling groups, in order to provide a higher level of signal associated with each nucleotide, or a more consistent signal. In particular, by providing multiple fluorophores coupled to a single nucleotide, one can mitigate the impact of variations in any single label, e.g., blinking or bleaching, by virtue of the presence of additional fluorophores.

In addition to the advantages of multiple coupling, the compositions of the invention also provide advantages in situations where one is desirous of shielding the effects of the functional group from other reaction components. For example, in some cases, fluorescently labeled nucleotides have been shown to cause damaging effects to polymerase enzymes when those systems are illuminated during polymerase incorporation of such labeled nucleotides. In the compositions of the invention, the presence of the linking component provides an additional separation between the label portion of the overall composition, and the portion that reacts with other reaction components, e.g., the nucleotide. Further, depending upon the nature of the linking component, it may provide a buffering component for such effects, e.g., providing a sacrificial component for triplet state effects or other impacts of fluorophore excitation and photo-induced damage. Additionally, one may incorporate additional functional components within the linking group. For example, with respect to the issue of triplet state effects and photo-induced damage, one may include triplet state quenchers and/or other photo-induced damage mitigating agents within the linking group; Examples of inclusion of triplet state quenchers into linker molecules have been described in, e.g., U.S. Patent Application Nos. 61/026,992 filed Feb. 7, 2008; and Ser. No. 12/367,411, filed Feb. 6, 2009, the full disclosures of which are hereby incorporated herein by reference in their entireties for all purposes. Further examples of photo-induced damage mitigating agents that may be included in linger molecules are provide Patent Publication No. 20070128133 and 20070161017; and U.S. Patent Application Nos. 61/116,048, filed Nov. 19, 2008, and Ser. No. 12/622,375, filed Nov. 19, 2009, entitled "Photo-induced Damage Mitigating Agents and Preparation and Methods of Use Thereof," the full disclosures of which are hereby incorporated herein by reference in their entireties for all purposes.

In at least one aspect, the linkage may comprise a biotin-avidin linkage (which, as used herein includes, e.g., avidin, streptavidin, neutravidin, or a biotin-binding subunit or derivative thereof). In exemplary operation, one component of the biotin-avidin pair, e.g., biotin, is coupled to the polyphosphate chain of the nucleotide, while the other component, e.g., avidin, is coupled to the functional group. Upon mixing the function group with the nucleotide group, the affinity binding of biotin and avidin links the functional group to the nucleotide through a non-covalent linkage. As will be appreciated, avidin comprises a tetrameric structure whereby a single avidin, streptavidin or neutravidin group can couple with up to four biotin groups. As such, use of an avidin group as one component of the linkage provides the multivalent attachment opportunities described above. Such multivalent structure could permit the attachment of a single functional group to multiple nucleoside polyphosphates, or alternatively and preferably, multiple functional groups to a single nucleoside polyphosphate. As will be appreciated, the four functional groups provided, may comprise a single type of functional group, to amplify the presence of such functional group, e.g., as in a single type fluorescent group. In particular, a single nucleotide molecule could be labeled with up to four different fluorophores to increase the emission output of the molecule. Likewise, because emission issues associated with a single fluorophore molecule, e.g., photobleaching, blinking, etc., would be substantially mitigated through the presence of multiple fluorophore molecules.

Alternatively, the functional groups may comprise a mixture of different types of functional groups that provide alternative functionalities as a mixture. For example, in some embodiments, donor and acceptor fluorophores may be attached to a single nucleotide to provide a fluorescent resonant energy transfer pair, as further described above. Alternatively, nucleotides may be provided with mixed emission profiles, e.g., using two distinct fluorophores, to provide greater flexibility in labeling without the need to expand the excitation spectrum of the desired application, e.g., using two distinct labels to label up to three different nucleotides.

Figure 2:
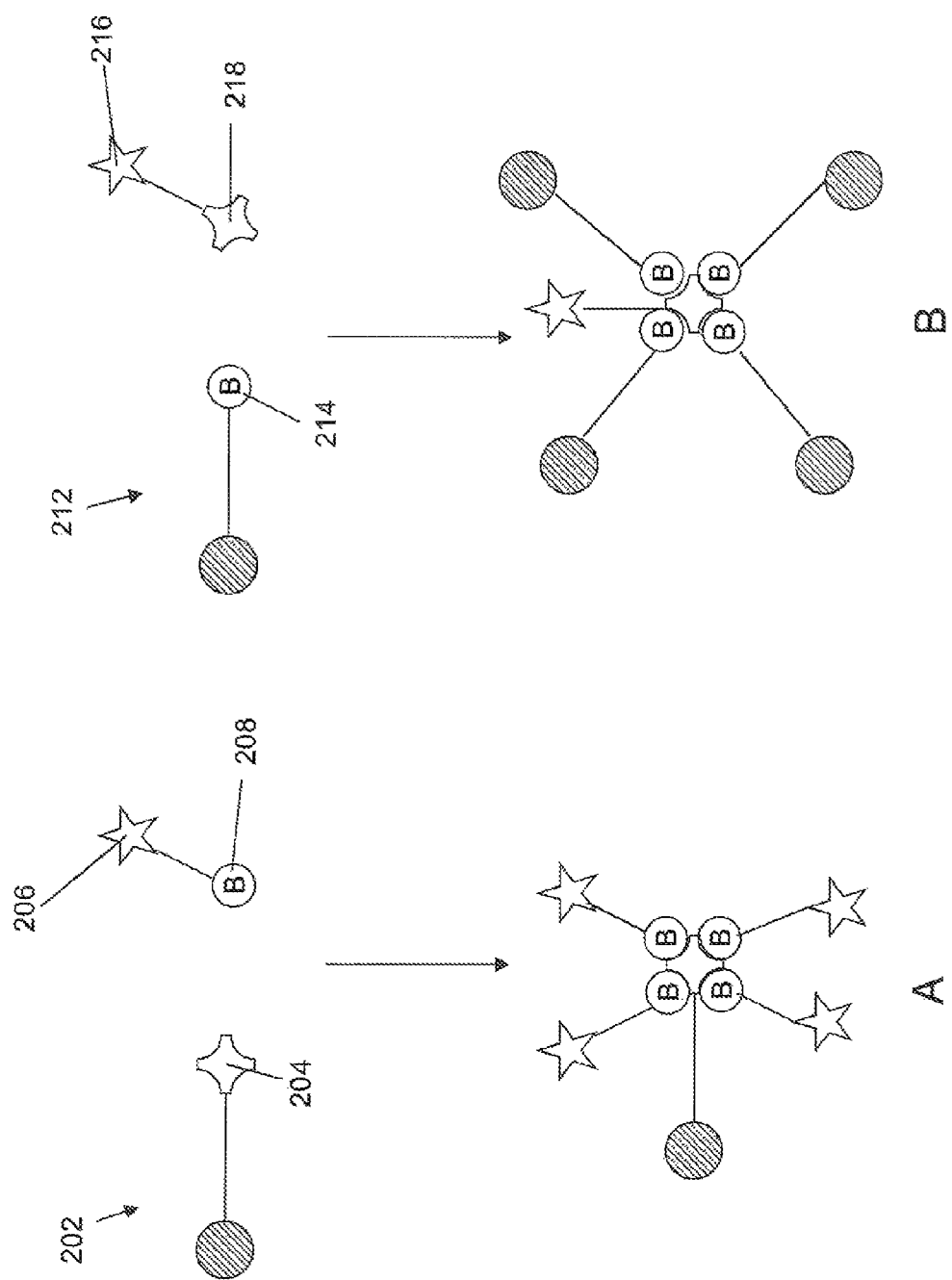
FIG. 2 schematically illustrates a multivalent modular composition according to the invention.

An example of a nucleotide structure of the invention employing a multivalent avidin/biotin linkage is schematically illustrated in FIG. 2. In particular, as shown in Panel A, a nucleotide analog 202 is provided with an avidin linkage group 204, having tetravalent binding capability. The nucleotide analog is combined with a functional group 206 that is coupled to a biotin group 208. The resulting compound 210 includes the nucleotide analog 202 bearing up to four functional groups 206. In an alternative configuration, shown in Panel B, the nucleotide analog 212 is coupled to the biotin group 214. The nucleotide analog is coupled to a functional group 216 that is coupled to an avidin group 218. Because the tetravalent avidin group 218 is provided upon the functional group 216, it permits up to four nucleotide analogs 212 to associate with a single functional group 216.

Figure 3:
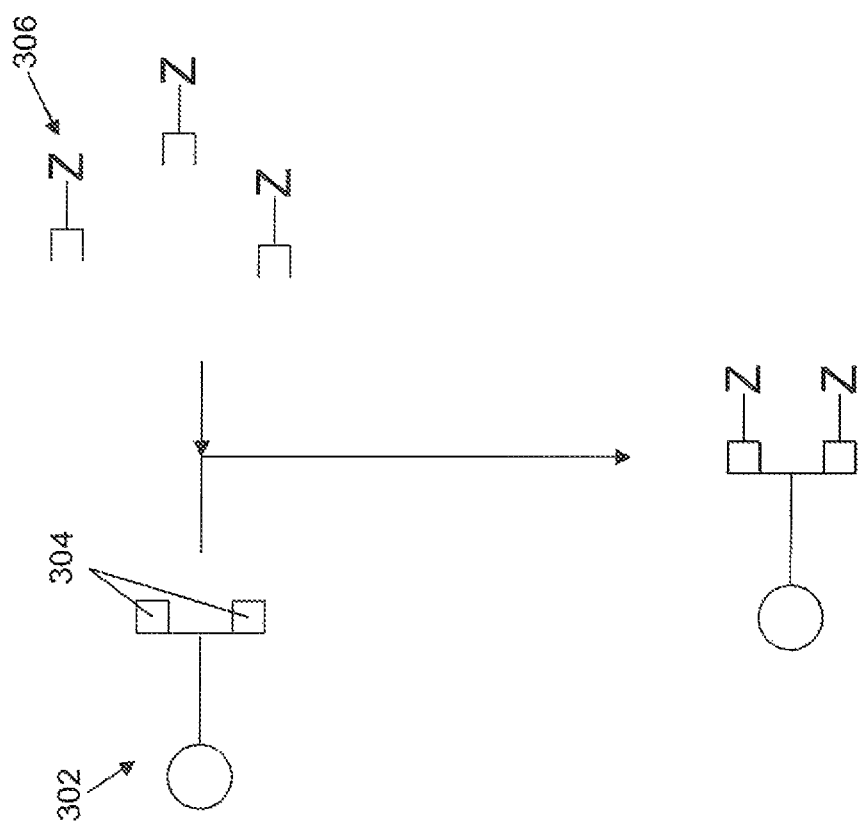
FIG. 3 schematically illustrates a multivalent composition that includes selectivity for the attachment of functional groups.

In still further variations, the compositions may include multiple linkage groups (as opposed to or in addition to single multivalent linkage groups). These linkage groups may comprise a single type of linkage group or they may comprise combinations of configurable linkage groups, which may be employed to attach multiple different functional groups, e.g., detectable labels. One example of such a multi-linkage configuration is illustrated in FIG. 3. As shown, a nucleotide analog 302 is provided with multiple linkage groups 304. Upon combination of the nucleotide analog with the functional groups bearing the complementary linkage group 306, the resulting functionalized nucleotide 308 bears multiple functional groups. Such multiply functionalized nucleotides may, as noted elsewhere herein, provide multiple label groups to amplify a detectable signal associated with the nucleotide, or otherwise amplify the effect of the functional group, e.g., providing greater electrical charge, greater changes in hydrophobicity/hydrophilicity, etc.

In an alternative configuration, different linkage components may be employed on a given nucleotide composition. For example, two different linking groups may be coupled to a single nucleoside polyphosphate in order to provide selective capability to add different types of functional groups. Examples of such multiple linking groups include a nucleoside polyphosphate bearing a biotin or avidin linking group, and also including a second type of linking group, e.g., an epitope, nucleic acid, etc. In one particular example, a first type of linking group, such as a biotin, avidin or the like, that provides the ability to couple a first functional group, e.g., a first dye label, may be coupled to the nucleoside phosphate portion of the composition through another type of linking group, e.g., a single stranded nucleic acid, that can function as a second linking site to link a second and distinct functional group, e.g., a second dye label.

Figure 4:
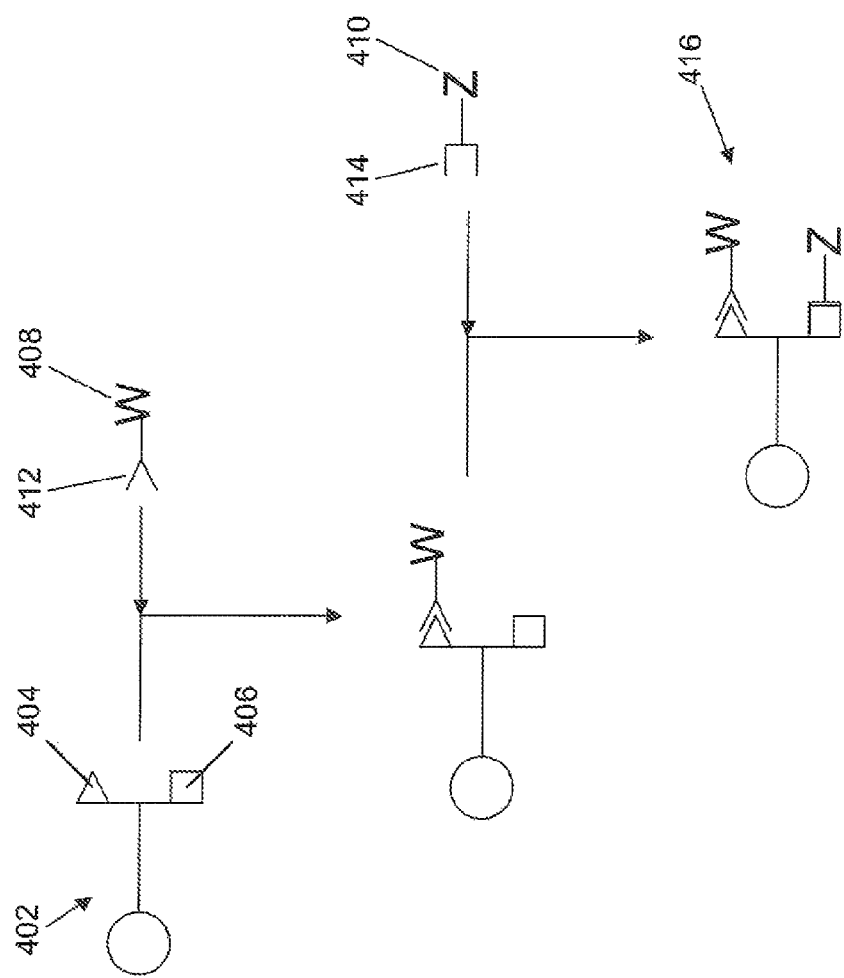
FIG. 4 schematically illustrates the use of tetravalent linkage groups in accordance with the invention.
Figure 5:
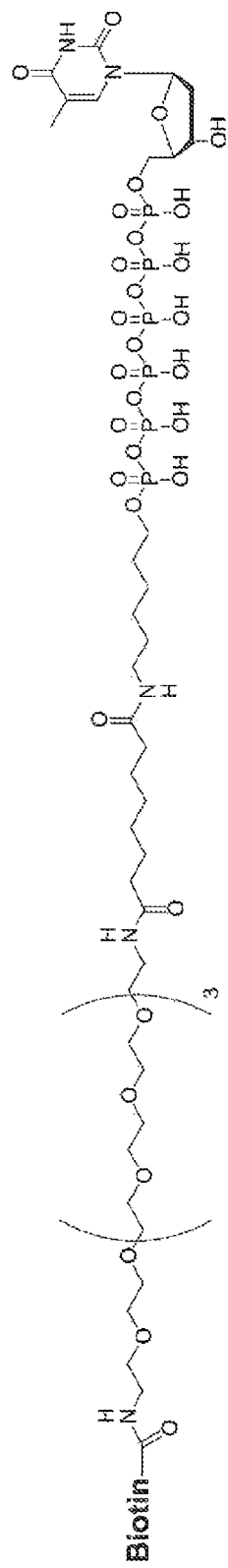
FIG. 5 shows an exemplary nucleotide analog composition including a biotin linking group.

Because each linking group is based upon a different affinity, one can selectively add the different, functional groups to the appropriate linking group through the use of the complements to the linking groups. An example of a nucleotide composition bearing such different linkage groups is schematically illustrated in FIG. 4. As shown, a nucleotide analog 402 is provided with multiple linkage groups including at least two different types of linkage groups having different affinity binding partners, e.g., linkage groups 404 and 406. The different functional groups, e.g., groups 408 and 410, are each provided with a different complementary linkage group (e.g., linkage groups 412 and 414, respectively), to one of the groups on the nucleotide composition. Upon contacting the nucleotide composition with each of the functional groups, it results in a bifunctionally coupled nucleotide analog 416. As noted, because each of the linkage groups relies upon a different affinity, it permits selective labeling of a nucleotide with differing functional groups. Such different functionalization may provide multiple optically detectable properties, e.g., different fluorescent labels having different excitation and/or emission spectra, or it may provide interactive labeling components, e.g., energy donor acceptor pairs fro, e.g., FRET-based fluorescent labeling, or the like. A variety of different functional groups may be readily coupled to the nucleotide analog, including intermediate functionalization, such as providing further selectivity for labeling or other modification.

As will be appreciated, the availability of a configurable, cassette approach to providing functional groups on nucleotides will lend itself particularly well to automated systems that are performing a desired application. In particular, based upon the desired characteristics of the nucleotide compositions for a given application, one can configure a system to automatically select the desired nucleotide component for coupling to the desired functional component. Because such coupling is based upon a non-covalent attachment, it can be carried out as an initial process step that precedes the use of the composition in the desired application. For example, where one is employing fluorescently labeled nucleotides in a sequencing application, one can configure the system to mix each of the different types of nucleotide components with a particular desired labeling component, e.g., having differing spectral characteristics and/or differing structural characteristics. The system would then dispense each component from an appropriate source of such components into a mixing vessel under conditions that promote the coupling reaction. The resulting reagents would then be dispensed into the desired sequencing reaction mixture. In some cases, intermediate steps may be included to reduce the level of a particular free component, but this will not always be required. For example in certain single molecule sequencing reactions, free labeling components will not provide any meaningful background signals, and thus would riot need to be removed prior to use in the sequencing reaction.(See, e.g., U.S. Pat. No. 6,917,726).

As noted previously, the compositions of the invention are particularly useful in a wide variety of different applications but have particular utility in nucleic acid analyses, and particularly, nucleic acid sequence analyses.

EXAMPLES

Compositions of the invention were prepared and evaluated in an exemplary application. Synthesis of the biotin-linked deoxynucleoside hexaphosphates (dN6P) was carried out as follows: 3 µMoles of Biotin-PEG12-NHS (Quanta Biodesign) was dissolved in 100 µl water. This was added to 1 µMole aminohexyl dN6P dissolved in 100 µl 50 mM NaHCO$_3$. After 2 hours the biotinylated product was purified by ion exchange chromatography. The structure of the resulting compound is illustrated in FIG. 4.

Streptavidin labeled with AlexaFluor® 568 ("A568SAv") fluorescent dye was purchased from Invitrogen Inc. (Carlsbad, Calif.), The A568-SAv was linked to the biotinylated nucleotide by incubation of the two compounds at a 1:3 molar ratio for 1 hour on ice. Excess biotin (10× molar over A568-SAv) was then added to block any remaining free biotin-binding sites on the protein. The labeled nucleoside hexaphosphate was then used in a single-molecule sequencing by incorporation process, employing an immobilized strand displacing DNA polymerase within an observation volume of a zero mode waveguide array. The polymerase was complexed with a template arid primer, sequence, where the template was made up of alternating blocks of A and C bases. The reaction was initiated and monitored using a high multiplex confocal fluorospectrometer (See, e.g., Lundquist et al., Optics Letters (2008), Vol. 33, Issue 9, pp. 1026-1028). Sequence data was obtained which shows that A568-SAv-Biotin-dT6P can be detected-as pulses in the sequence with good signal-to-noise, and that using two similar constructs for A568-SAv-dT6P and A648-SAv-dG6P also showed ready incorporation by the polymerase system.

Figure 6A:
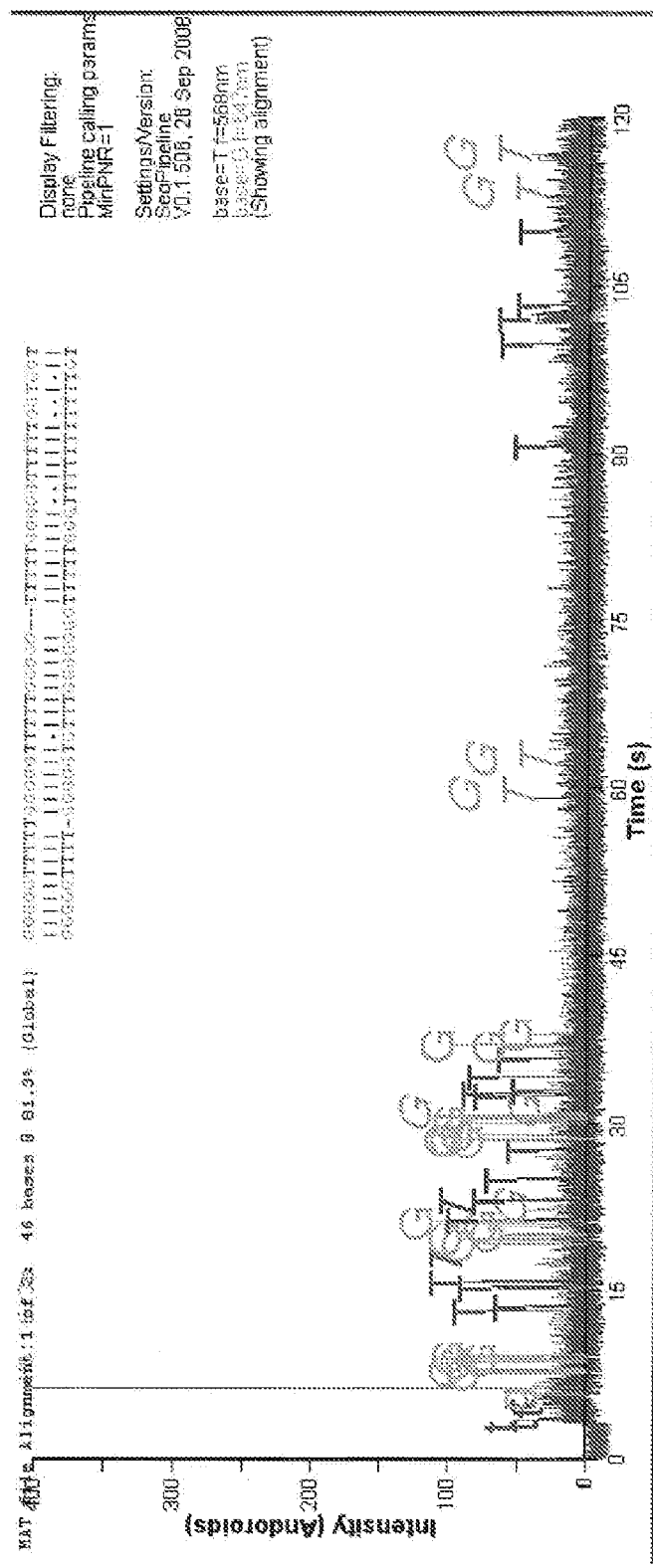
FIG. 6 shows real-time single molecule sequence data using nucleotide analog compositions like that shown in FIG. 5.
Figure 6B:
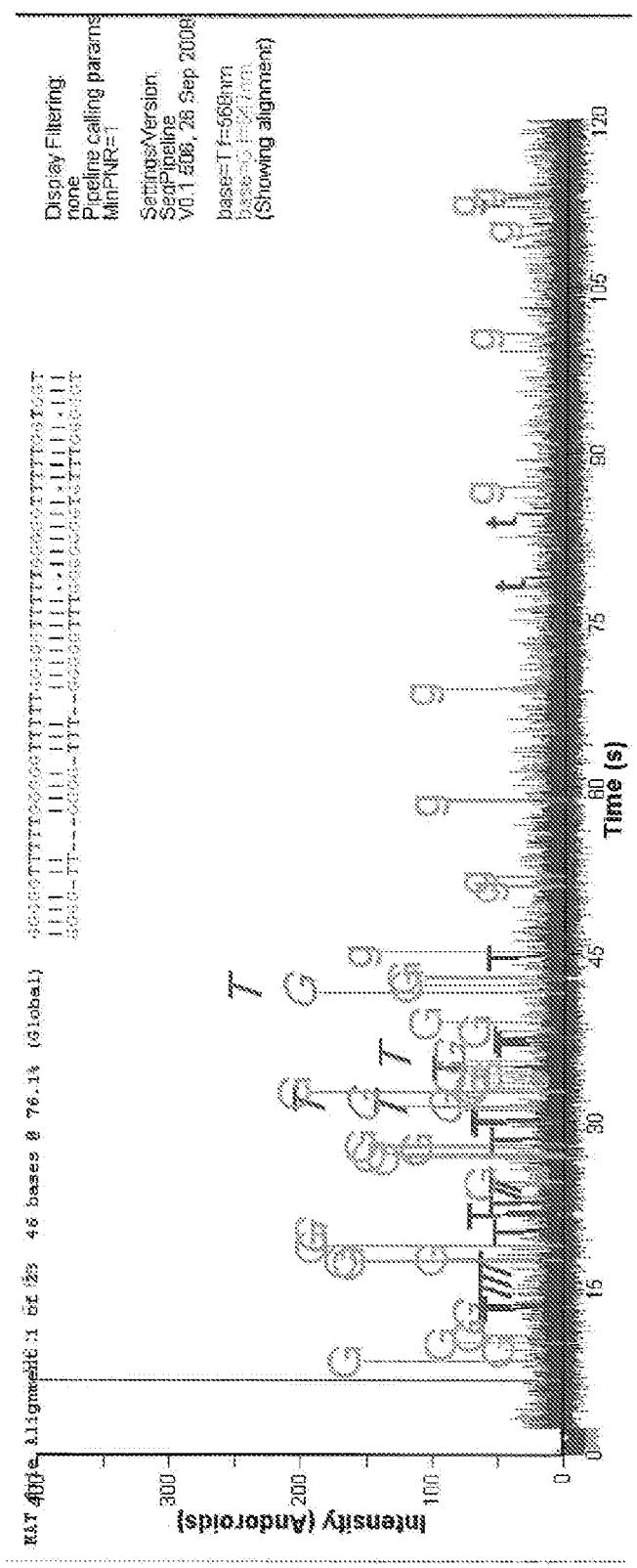
Figure 6C:
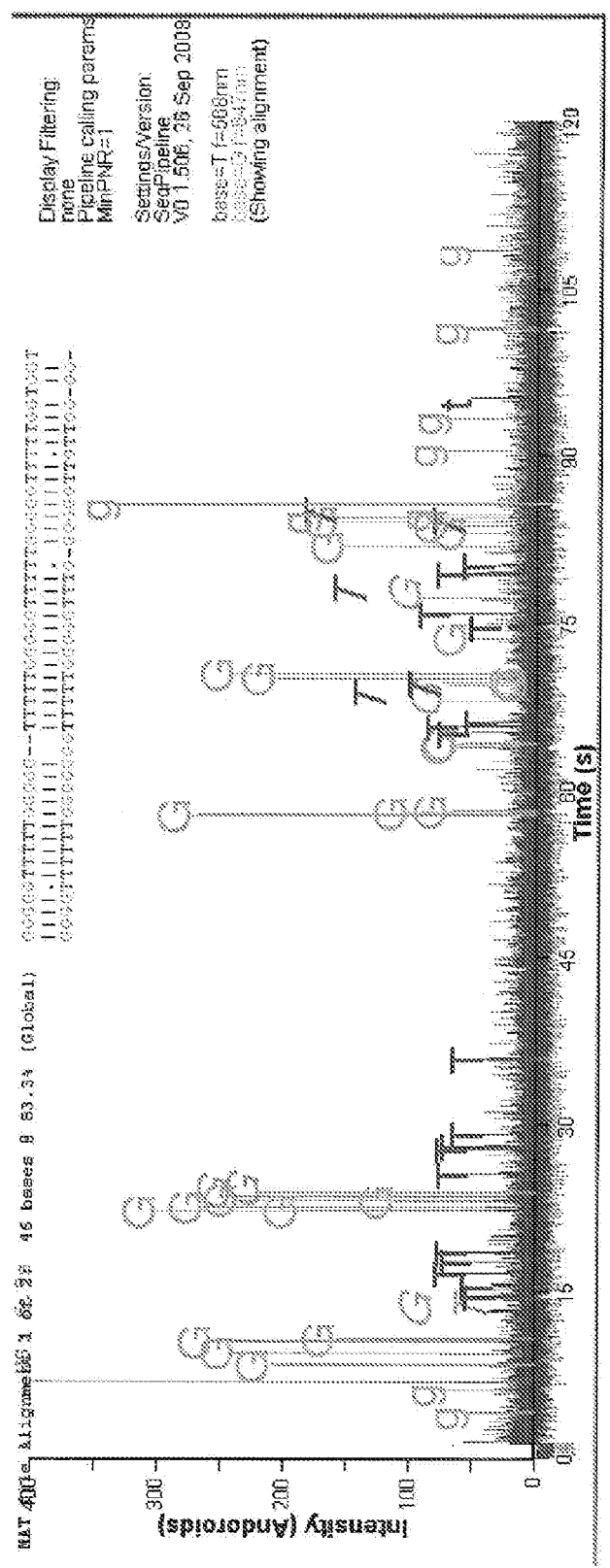

FIGS. 6A, B and C show detection of incorporation of: A568-SAv-Biotin-dT6P in conjunction with A648-dG6P (FIG. 6A), A568-dT6P in conjunction with A648-SAv-dG6P (FIG. 6B), and A568-SAv-Biotin-dT6P in conjunction with A648-SAv-dG6P (FIG. 6C). In all cases, the incorporation of blocks of T and G analogs is evident and detected.

Although described in some detail for purposes of illustration, it will be readily appreciated that the above description is not intended to be restrictive and a number of variations known or appreciated by those of skill in the art may be practiced, within the scope of present invention. All publications mentioned herein are cited for the purpose of describing and disclosing reagents, methodologies and concepts that may be used in connection with the present invention. Nothing herein is to be construed as ah admission that these references are prior art in relation to the inventions described herein. To the extent hot already expressly incorporated herein, all published references and patent documents referred to in this disclosure are incorporated herein by reference in their entirety for all purposes.

We claim:

1. A composition comprising a reaction component coupled to a fluorescent label through a non-covalent linkage component configured to provide a separation between the fluorescent label and the reaction component, wherein the reaction component comprises a nucleoside polyphosphate, and further wherein the fluorescent label causes photo-induced damage to an enzyme interacting with the reaction component under excitation illumination in the absence of the separation provided by the non-covalent linkage component, which shields the enzyme from the fluorescent label during interaction between the enzyme and the reaction component.

2. The composition of claim 1, wherein the linkage component comprises a sacrificial component that is impacted by the photo-induced damage, thereby shielding the enzyme.

3. The composition of claim 1, wherein the linkage component comprises a triplet state quencher.

4. The composition of claim 1, wherein the linkage component is a multivalent linkage group.

```
                      SEQUENCE LISTING

<160> NUMBER OF SEQ ID NOS: 4

<210> SEQ ID NO 1
<211> LENGTH: 46
<212> TYPE: DNA
<213> ORGANISM: Artificial Sequence
<220> FEATURE:
<223> OTHER INFORMATION: Nucleic acid strand complementary to template
      with alternating blocks of A and C bases

<400> SEQUENCE: 1
gggggttttt gggggttttt gggggttttt gggggttttt ggtggt                      46

<210> SEQ ID NO 2
<211> LENGTH: 47
<212> TYPE: DNA
<213> ORGANISM: Artificial Sequence
<220> FEATURE:
<223> OTHER INFORMATION: Nucleic acid strand synthesized using template
      with alternating blocks of A and C bases

<400> SEQUENCE: 2
gggggttttg gggtgtttg ggggggtttt tgggttttt tttttgt                       47

<210> SEQ ID NO 3
<211> LENGTH: 39
<212> TYPE: DNA
<213> ORGANISM: Artificial Sequence
<220> FEATURE:
<223> OTHER INFORMATION: Nucleic acid strand synthesized using template
      with alternating blocks of A and C bases

<400> SEQUENCE: 3
ggggttgggg tttgggggtt tggggggtg tttggggt                                39

<210> SEQ ID NO 4
<211> LENGTH: 45
<212> TYPE: DNA
<213> ORGANISM: Artificial Sequence
<220> FEATURE:
<223> OTHER INFORMATION: Nucleic acid strand synthesized using template
      with alternating blocks of A and C bases

<400> SEQUENCE: 4
ggggtttttt ggggggggttt ttggggttt ggggggttgt tgggg                       45
```

5. The composition of claim 4, wherein the multivalent linkage group couples multiple functional groups to the reaction component, wherein the fluorescent label is among the multiple functional groups.

6. The composition of claim 4, wherein the multivalent linkage group is selected from avidin, streptavidin, and neutravidin.

7. The composition of claim 4, wherein the fluorescent label comprises multiple fluorophores, and the multivalent linkage group is coupled to the multiple fluorophores.

8. The composition of claim 4, wherein the multivalent linkage group is coupled to both the fluorescent label and to a photo-induced damage mitigating agent.

9. The composition of claim 1, wherein the fluorescent label is a FRET label.

10. The composition of claim 1, wherein the linkage component is coupled to a phosphate group of the nucleoside polyphosphate.

11. The composition of claim 10, wherein the linkage component is coupled to a phosphate group of the nucleoside polyphosphate by a non-covalent linkage.

12. The composition of claim 1, wherein the enzyme is a polymerase enzyme.

13. A method of shielding an enzyme from photo-induced damage within a reaction mixture, the method comprising dispensing the composition of claim 1 into the reaction mixture.

14. The composition of claim 1, further dispensed into a reaction mixture comprising the enzyme.

\* \* \* \* \*